United States Patent [19]

Kralovic

[11] Patent Number: 5,374,394
[45] Date of Patent: Dec. 20, 1994

[54] MEDICAL WASTE DECONTAMINATION

[75] Inventor: Raymond C. Kralovic, Ashtabula, Ohio

[73] Assignee: Steris Corporation, Mentor, Ohio

[21] Appl. No.: 23,048

[22] Filed: Feb. 25, 1993

Related U.S. Application Data

[63] Continuation-in-part of Ser. No. 793,589, Nov. 18, 1991, Pat. No. 5,209,909, which is a continuation-in-part of Ser. No. 681,118, Apr. 5, 1991, Pat. No. 5,217,698, and Ser. No. 342,189, Apr. 24, 1989, Pat. No. 5,116,575, said Ser. No. 681,118, is a continuation-in-part of Ser. No. 342,189, Apr. 24, 1989, and Ser. No. 349,304, May 9, 1989, Pat. No. 5,091,343, which is a continuation-in-part of Ser. No. 140,388, Jan. 4, 1988, Pat. No. 4,892,706, said Ser. No. 342,189, is a continuation-in-part of Ser. No. 229,917, Aug. 8, 1988, Pat. No. 5,077,008, which is a continuation-in-part of Ser. No. 140,388, Jan. 4, 1988, and Ser. No. 165,189, Mar. 17, 1988, Pat. No. 5,037,623, each is a continuation-in-part of Ser. No. 826,730, Feb. 6, 1986, Pat. No. 4,731,222.

[51] Int. Cl.$^5$ .................................................. A61L 2/18
[52] U.S. Cl. ......................................... 422/28; 422/32; 422/292; 422/294
[58] Field of Search ................. 422/28, 34, 37, 32, 422/292, 294

[56] References Cited

U.S. PATENT DOCUMENTS

| | | | |
|---|---|---|---|
| 4,578,185 | 3/1986 | Wilson et al. | 210/85 |
| 4,618,103 | 10/1986 | Wilson et al. | 241/41 |
| 4,619,409 | 10/1986 | Harper et al. | 241/38 |
| 5,054,696 | 10/1991 | Mennel et al. | 241/34 |
| 5,089,228 | 2/1992 | Meijer | 422/37 |

Primary Examiner—Lyle A. Alexander
Attorney, Agent, or Firm—Fay, Sharpe, Beall, Fagan, Minnich & McKee

[57] ABSTRACT

A bag (86) of medical wastes is inserted into a chamber (12) that contains a grinder (20). A package (48) is placed unopened in the chamber with the medical wastes. A selected volume of a dilutant such as water is added to the chamber (40, 42). The chamber is closed and the grinder operated for a selected duration. The grinder grinds the packaging, disposing of the packaging and permitting contained dry reagents (56, 58) such as acetylsalicylic acid and perborate to react with the dilutant, forming a peracetic acid solution or permitting a sterilant concentrate (70) to form an anti-microbial solution with the dilutant. The grinder continues to grind the packaging and the medical wastes into fine particulates forming a slurry with the peracetic acid solution. The continued operation of the grinder assures that the anti-microbial solution contacts all surfaces of the waste. In this manner, the medical wastes are microbially decontaminated. A color indicator (60, 78) is included with the packaging to provide a color indication as to whether the anti-microbial reaction is complete. For example, a Gentian Violet may be provided which fades to white to indicate completion of the decontamination process. Once decontaminated, the slurry is removed from the chamber and disposed of as non-contaminated waste materials. Optionally, fragrances and deodorants may be included in the package.

6 Claims, 3 Drawing Sheets

MEDICAL WASTE DECONTAMINATION

This application is a continuation-in-part of U.S. application Ser. No. 07/793,589, filed Nov. 18, 1991 now U.S. Pat. No. 5,209,909. U.S. application Ser. No. 07/793,589 is a continuation-in-part of U.S. application Ser. No. 07/681,118, filed Apr. 5, 1991 now U.S. Pat. No, 5,217,698 and U.S. application Ser. No. 07/342,189, filed Apr. 24, 1989 now U.S. Pat. No. 5,116,575.

U.S. application Ser. No. 07/681,118, is a continuation-in-part of U.S. application Ser. No. 349,304, filed May 9, 1989 now U.S. Pat. No. 5,091,343 and said U.S. application Ser. No. 07/342,189 now U.S. Pat. No. 5,116,575. U.S. application Ser. No. 349,304 is a continuation-in-part of U.S. application Ser. No. 140,388, filed Jan. 4, 1988, now U.S. Pat. No. 4,892,706. U.S. application Ser. No. 07/342,189 is a continuation-in-part of U.S. application Ser. No. 229,917, filed Aug. 8, 1988 now U.S. Pat No. 5,077,008, which is a continuation-in-part of said U.S. application Ser. No. 140,388 and U.S. application Ser. No. 07/165,189, now U.S. Pat. No. 5,037,623, filed Mar. 17, 1988, which in turn are continuations-in-part of U.S. application Ser. No. 826,730, filed Feb. 6, 1986, now U.S. Pat. No. 4,731,222.

BACKGROUND OF THE INVENTION

The present invention relates to the decontamination arts. It finds particular application in conjunction with the sterilizing or disinfecting of medical wastes and will be described with particular reference thereto. However, it is to be appreciated that the present invention will also find application in connection with the disposal of any products having potentially harmful microorganisms.

Microbial decontamination connotes the removal of hazardous or unwanted bacteria, mold spores, and other pathogenic life forms. Disinfection connotes the absence of pathogenic life forms. Sterilization connotes the absence of all life forms, whether pathogenic or not.

Heretofore, medical waste such as used syringes, petri dishes and culture media, vials, and other equipment which has come in contact with substances which might potentially carry pathogenic organisms have been subject to elaborate and expensive waste disposal procedures. Traditionally, these wastes were incinerated at sufficiently high temperatures that the pathogenic organisms were killed. However, incinerators tend to be a source of air pollution and are being closed.

Other medical wastes are sterilized in a steam autoclave. Autoclave sterilization is a relatively time consuming and expensive procedure, particularly for waste materials.

Another technique for disposing of medical wastes is to grind the wastes with water into a slurry. Bound iodine solutions are commonly added to presumably kill pathogenic organisms. However, one of the problems with this system is providing assurance that the pathogenic organisms are killed.

In accordance with the present invention, a new and improved system for decontaminating medical waste is provided.

SUMMARY OF THE INVENTION

In accordance with one aspect of the present invention, a method is provided for safely disposing of medical wastes. Medical wastes are disposed in a chamber of a grinding apparatus. Two components which react in the presence of a dilutant to form an anti-microbial material are sealed in separate packets in premeasured doses. The packets containing the two or more components are put into the grinder unopened along with the medical waste. Water or other fluid is added to the grinder as necessary. The grinder grinds and mixes the medical waste, severing the sealed packets allowing the premeasured doses of the two reagents to react and form an anti-microbial solution. The grinding process completely intermixes the formed anti-microbial solution and the waste. After a selected duration sufficient for the anti-microbial solution to disinfect the waste, the grinding chamber is emptied. Because the ground waste has now been microbially decontaminated, it is no longer hazardous waste. Rather, it can be disposed of like any other waste.

In accordance with another aspect of the present invention, the components react to form a strong oxidant with a relatively short half life.

The short half life of the microbial decontaminate can be adjusted such that decontaminate remains active long enough to render the waste harmless but does not create a separate environmental toxin.

In accordance with another aspect of the present invention, a color indicator means is sealed in a stored compartment. The sealed compartment of the color indicator, the medical wastes, and compartments with either an anti-microbial agent or components which react to form an anti-microbial agent are inserted into a grinder with water, as necessary. The grinder is actuated to open the compartments containing the indicator and the anti-microbial agent or anti-microbial agent components. After the grinding process, the color of the ground waste slurry is checked for an indication that the waste has been microbially decontaminated.

In accordance with a more limited aspect of the present invention, the anti-microbial agent is a strong oxidant or components which react to form a strong oxidant and the indicator is Gentian Violet, which changes from violet to white under a combination of time, temperature, and acid concentration—the three factors which contribute to microbial decontamination.

In accordance with another aspect of the present invention, a deodorizing agent or a fragrance is included in the packaged chemicals.

One advantage of the present invention is that it reliably microbially decontaminates medical waste.

Another advantage of the present invention is that it prevents direct user contact with concentrated anti-microbial agents.

Another advantage of the present invention is that it reduces the potential for operator error in the sterilization of microbially decontaminated waste materials.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
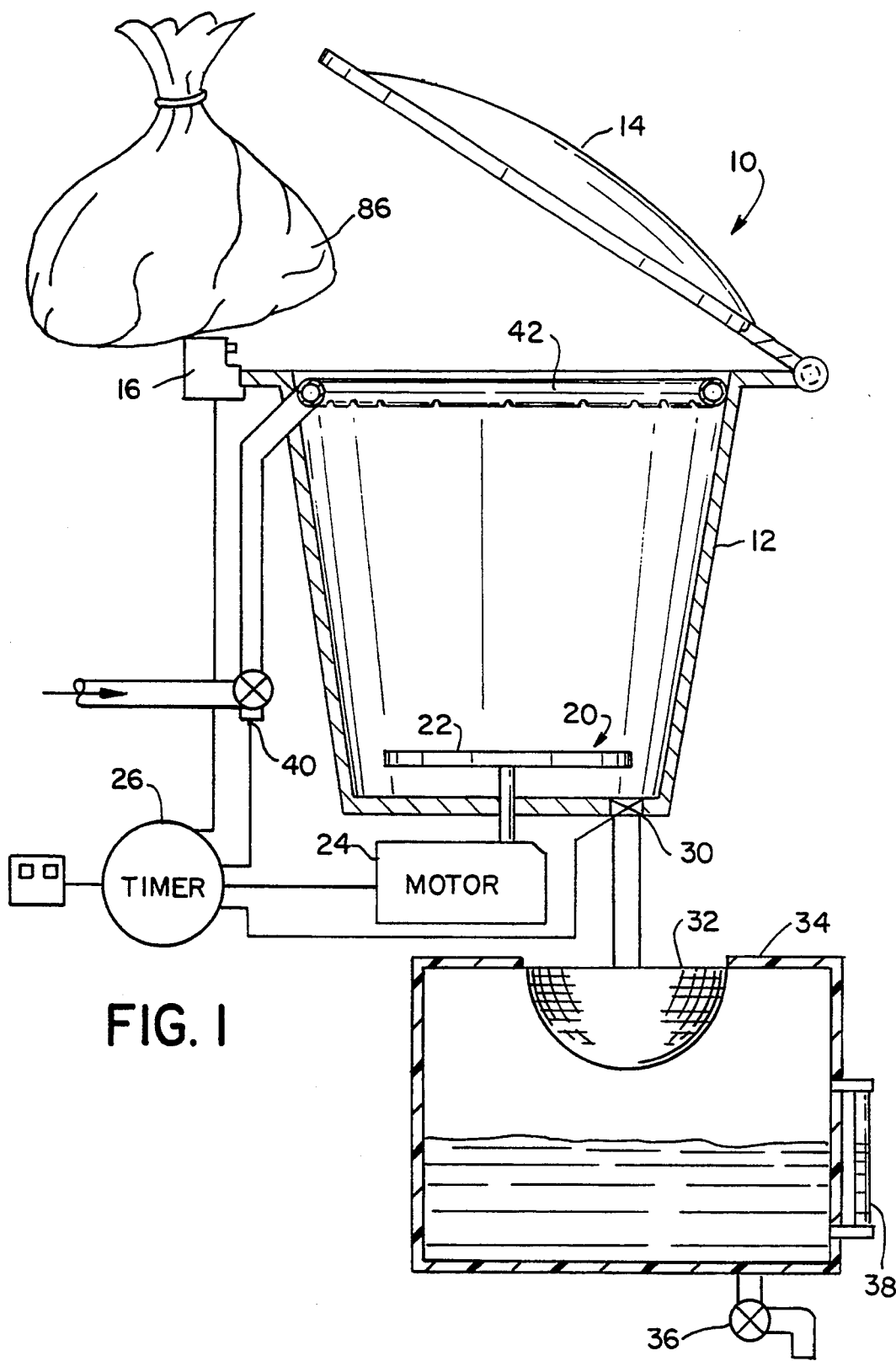
FIG. 1 is a diagrammatic illustration of a waste grinding system in accordance with the present invention.

A waste disposal system 10 includes a body portion 12 which defines an interior chamber and an openable lid 14 for selectively sealing the chamber. The lid and body portion are constructed of or are at least lined with a structurally strong, relatively inert material, such as stainless steel. A latching means 16 selectively latches the lid in a fluid-tight sealed relationship with the body portion.

A grinding means 20 is disposed inside of the body portion internal chamber adjacent the bottom. The grinding means 20 includes a shaft which supports a plurality of blades 22 of sufficiently hardened material to shatter and grind glass, metal cannulas, plastics, and the like. The blades are also designed to shred plastic bags and other flexible light-weight plastic. A motor and gear box means 24 rotates the blades of the grinder means at a relatively high rate of speed. A timer means 26 is selectively actuated by the operator to cause the motor 24 to run for a selected duration. The duration is selected to be sufficient for (1) the grinding means 20 to completely grind received medical waste and (2) to cause a complete intermixing and reaction of the anti-microbial reagents. Preferably, the timer 26 is also interconnected with the latching means 16 to lock the lid latched whenever the motor is on to prevent inadvertent opening of the lid. Conversely, the latch means 16 can be interconnected with the timer 26 to cause the motor to stop immediately if the lid is opened.

After the selected grinding cycle and after a selected additional duration for the anti-microbial material to operate on any microbes, the timing means 26 opens a drain valve 30, draining the slurry of ground medical waste and anti-microbial solution into a straining means 32. The straining means catches and holds the particles of glass, metal, plastic, and the like which have been ground to a fine sand-like particulate. Fluid drains through the strainer 32 into a holding tank 34. A drain valve 36 enables the holding tank 34 to be drained periodically into a drain or other liquid disposal system. Optionally, a sight glass 38 is provided which enables the fill level and the color of the liquid in the holding tank to be monitored.

The timer 26 further operates a fluid valve 40 which admits tap water or other dilutant and rinse fluids into the system. A series of spray nozzles 42 around an upper periphery of the chamber 10 spray the interior of the chamber to rinse any residue through drain valve 30 into the strainer 32 and the holding tank 34. Optionally, the valve 40 may be opened at the beginning of the cycle for a duration selected to introduce a selected volume of fluid in the chamber 10 to enable the sterilant reagents to react and provide a selected concentration anti-microbial solution while providing the anti-microbial solution with mobility to reach all microbes.

Figure 2:
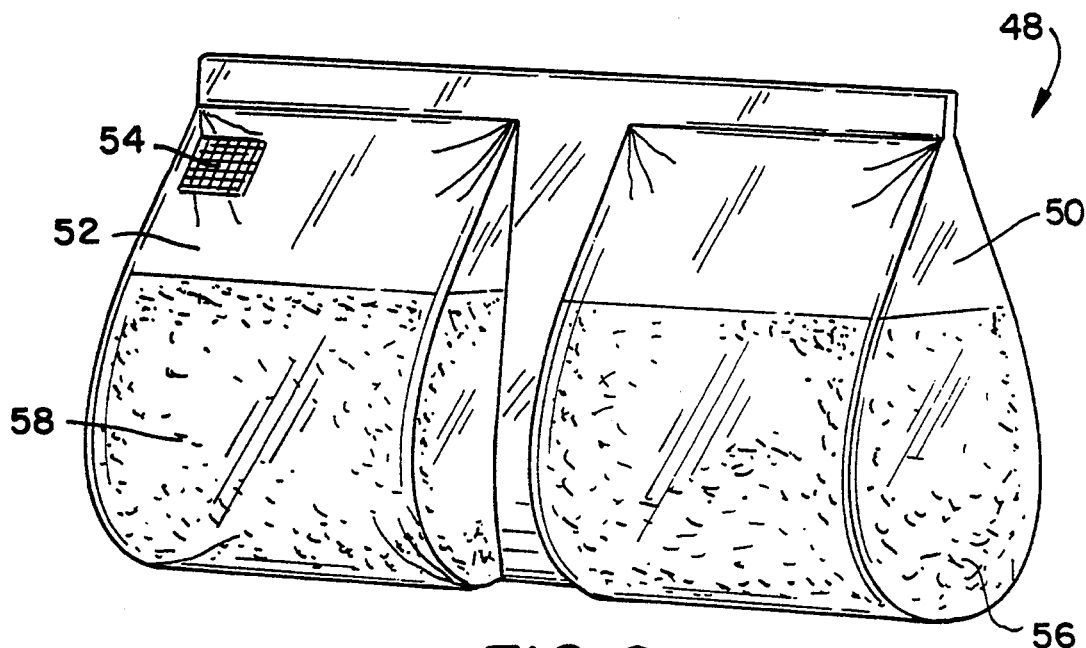
FIG. 2 is a perspective view of a microbial decontaminant packaged for use in conjunction with the device of FIG. 1.

With reference to FIG. 2, a closed package 48 holds the active reagents for making the anti-microbial solution. In the embodiment of FIG. 2, the package includes a first closed compartment 50 and a second closed compartment 52. The compartments 50, 52 are heat sealed from a flexible plastic sheet. The first and second compartments hold metered amounts of two reagents which react in water to form the sterilant solution. If one or both of the reagents off-gas, i.e., liberate a gas, a vent 54 is provided in the associated compartment. Preferably, the vent 54 permits gas to leave the compartment but inhibits moisture from entering, e.g., a check valve.

Figure 3:
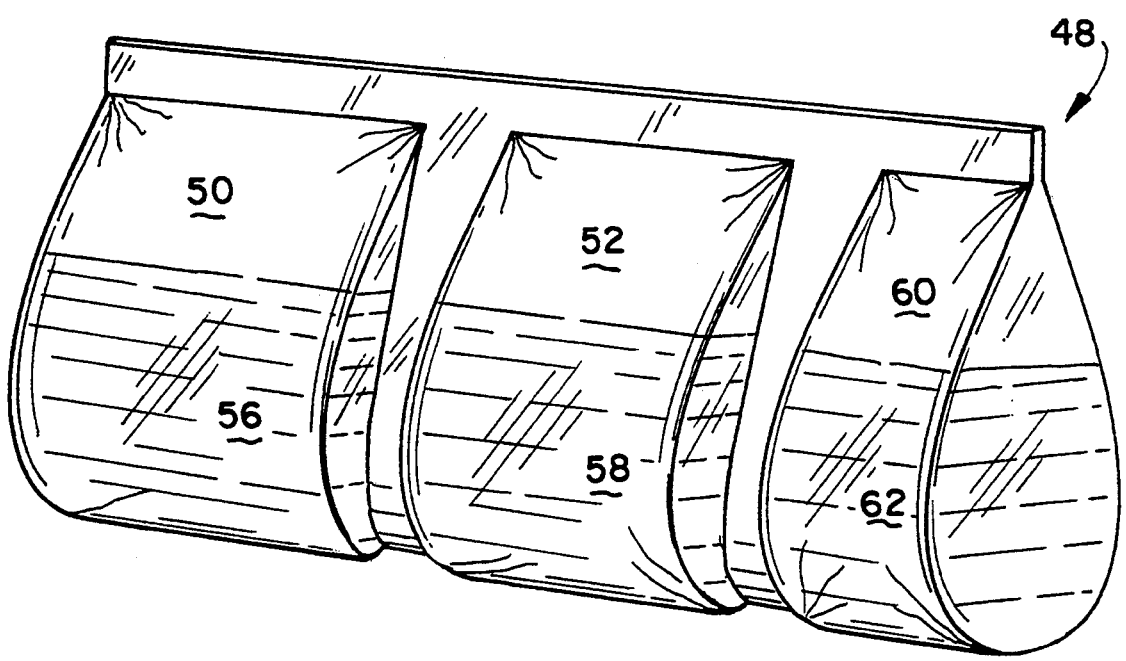
FIG. 3 is an alternate embodiment of packaging for the microbial decontaminant; and, FIG. 4 is a view in partial cross-section of yet other packaging for the microbial decontaminant and indicator.

In the preferred embodiment, one of the reagents includes a dry acid precursor 56, preferably acetylsalicylic acid. The other reagent includes is a persalt 58, preferably a sodium or other perborate in dry form. The acid precursor and persalt react in the presence of water to form sodium metaborate, peracetic acid, and salicylic acid. The volume of the dry reagents in the first and second compartments 50 and 52 and the volume of added water are coordinated such that a concentration of peracetic acid is achieved in the resultant solution sufficient to produce the desired anti-microbial effect. The peracetic acid is a strong oxidant and aggressive anti-microbial agent. The salicylic acid and any unreacted acetylsalicylic acid have anti-microbial properties as well. Wetting agents or detergents may also be added to improve the efficacy of the anti-microbial action. Optionally, anti-corrosives may be added, if necessary, to protect the grinding means 20 and the housing With reference to FIG. 3, the package preferably further includes a third container 60 which contains a color indicator such as Gentian Violet {4-{bis[p-(dimethylamino)phenyl]methylene}-2,5-cyclohexadien-1-ylidine}dimethylammonium chloride; hexamethylpararosaniline chloride; hexamethyl-p-rosaniline chloride. The Gentian Violet imparts a dark violet color to the slurry or solution, which violet color fades to white with a combination of time, temperature, and acid concentration. The concentration of Gentian Violet is selected such that the color fades to white if an appropriate amount of peracetic acid is generated during the grinding and any delay time before the drain valve is opened. In this manner, the color of the discharged fluid is indicative of whether peracetic acid of the appropriate concentration was formed and whether an appropriate temperature and duration were maintained for sterilization to occur.

Other oxidizing or antimicrobial agents can also be generated in situ, such as chlorine dioxide, chlorine, hydrogen peroxide, and mixtures thereof. More specifically, potassium chromates, sodium chloride, and phosphates may be mixed according to the following equation to produce a strong chlorine oxidant on the addition of water:

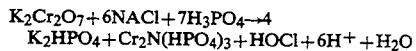
$$K_2Cr_2O_7 + 6NACl + 7H_3PO_4 \rightarrow$$
$$K_2HPO_4 + Cr_2N(HPO_4)_3 + HOCl + 6H^+ + H_2O$$

Optionally, excess dichromate and an organic corrosion inhibitor may be provided for improved buffering and corrosion inhibiting.

Hydrogen peroxide and an inorganic inhibitor can be generated:

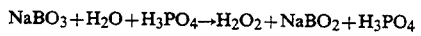
$$NaBO_3 + H_2O + H_3PO_4 \rightarrow H_2O_2 + NaBO_2 + H_3PO_4$$

Similarly, chlorine dioxide can be generated from powdered ingredients on the addition of water:

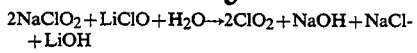

A mixed biocide system can be achieved by adding sodium chloride to the peracetic acid reaction to produce hypochlorous acid.

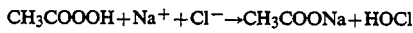

Excess peracetic acid is deliberately present such that both peracetic acid and hypochlorous acid are present in the biocidal solution.

Figure 4:
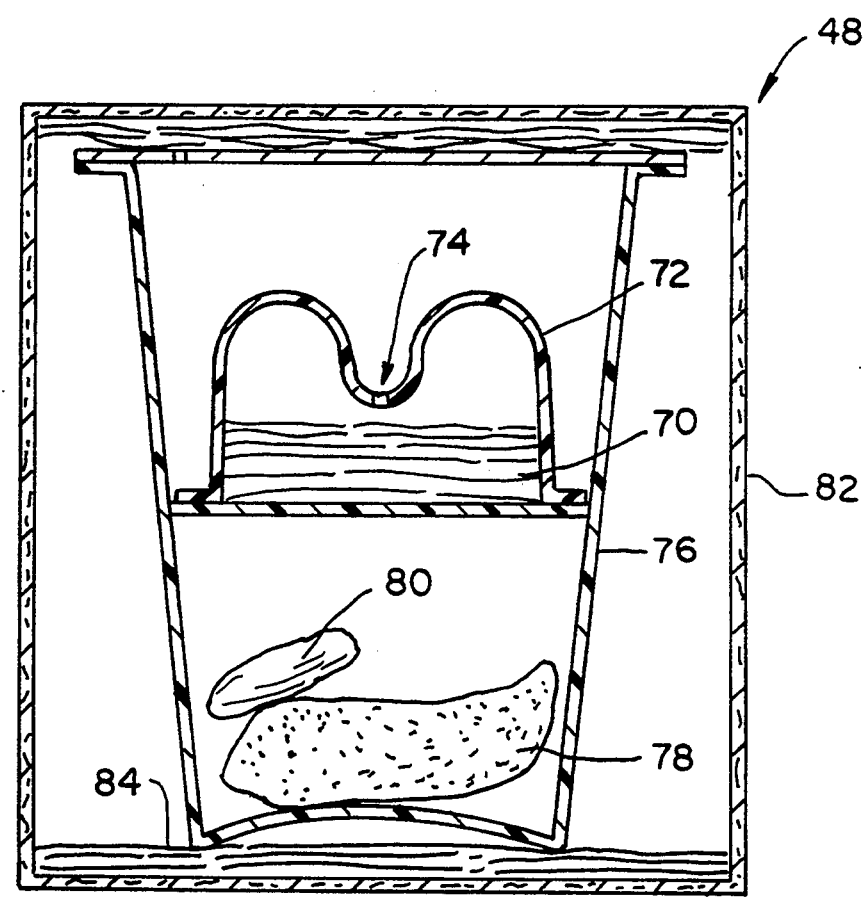

In some applications, the medical waste may contain chemicals which interfere with the reacting of the dry reagents. This is more apt to occur in medical laboratories where culture mediums and other chemicals are among the disposed wastes. In the embodiment of FIG. 4, the package 48 includes a concentrate of the anti-microbial agent, such as peracetic acid, in a liquid form 70. More specifically, the liquid sterilant concentrate is housed in an ampule 72. For peracetic acid and other anti-microbial agents which liberate gas, a vent aperture 74 is provided. In the preferred embodiment, the vent aperture 74 is disposed at the volumetric center of the ampule 72 which is only half filled with the anti-microbial liquid 70. The anti-microbial liquid is housed in a carrier or common container 76 which has a second compartment for holding a color indicator reagent 88, such as the Gentian Violet, a deodorant or fragrance 80, or the like.

The package 48 may further include a cardboard box 82 or other shipping container. Padding or cushioning materials 84 may be impregnated with the deodorant or fragrance or other reagents. The deodorant or fragrance is released as the packaging is ground by grinder 20.

In use, a plastic bag 86 containing the medical waste is placed in the chamber 12. The package 48 of the premeasured doses of anti-microbial agent are also placed in the chamber 12. The package 48 is not opened. Rather, the closed package is placed in an unopened condition within the chamber 10 to assure that the operator does not come into contact with potentially dangerous anti-microbial agents. The operator may add a preselected dose of water, e.g. a liter. The lid 14 is closed and latched. Preferably, the valve 40 is opened to meter the preselected dose of water into the chamber 12. The timer 26 causes the motor 24 to revolve the cutting blades 22 for a sufficient duration to assure that all medical waste and the package 48 is ground to a fine pulp or slurry, e.g. about three minutes depending on the volume of the chamber 10 and the grinding efficiency of the grinding means 20. The dry reagents may be added in the form of a pellet which is ground by the grinding means. The timing means then times a duration which is selected to insure that the anti-microbial solution formed has the contents of the package 48 has an adequate time to kill all pathogenic life forms, e.g. about ten minutes. This duration can be lengthened or shortened by using higher concentrations of the anti-microbial solution or by including buffering reagents which cause the reaction which forms the solution to progress more quickly or more slowly.

The valve 30 is opened and the slurry of ground and microbially decontaminated medical waste is discharged. The granular solids are held in the strainer 32 while the liquids drain into the holding tank 34. The operator checks the color of liquid in the holding tank 34 in the sight glass 38 to determine whether the color change indicative of the completion of the decontamination process has occurred. If decontamination is complete, the drain valve 36 may be opened and the decontaminated liquid waste discharged and disposed of as any non-contaminated liquid waste would be handled. If the liquid in the sight glass shows a color which leads the operator to question whether or not the liquid was completely decontaminated, the liquid and solids may be returned to the decontamination chamber with another package 48 of the sterilant and the process repeated. Alternately, another package 48 of the sterilant material can be added to the sterilant chamber 12 with the premeasured dose of water and the grinder 20 run for a short duration to make an anti-microbial solution. The valve 30 is opened such that the anti-microbial solution is drained through the solids and strainer 32 and into the liquid in the drain tank 34 to complete the sterilization process.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of decontaminating medical wastes, the method comprising:
    placing medical wastes in a chamber containing a grinder;
    placing a vented package which holds (i) a vented ampule containing a premeasured dose of liquid peracetic acid, (ii) a container of dry reagents, and (iii) a color indicator which changes color to indicate antimicrobial activity unopened in the chamber;
    adding a volume of liquid dilutant to the chamber;
    comminuting the wastes and the package in the chamber (i) releasing the liquid peracetic acid, the dry reagents, and the color indicator into the dilutant, (ii) comminuting the medical wastes and the package to a slurry, and (iii) mixing the liquid peracetic acid with the dilutant to form an anti-microbial peracetic acid solution, and (iv) intermixing the anti-microbial peracetic acid solution with all surfaces of solid components in the slurry, the anti-microbial peracetic acid solution having a sufficient concentration of peracetic acid to kill all pathogenic microorganisms in the medical waste;
    after comminuting, holding the slurry sealed in the chamber for a duration preselected to assure that the peracetic acid solution has sufficient time to operate on and kill the pathogenic microorganisms in the slurry;
    checking the color of the color indicator to assure antimicrobial activity;
    separating the anti-microbial peracetic acid solution from the solid components of the slurry.

2. A method of decontaminating biological wastes, the method comprising:
    placing biological wastes in a chamber containing a comminuting apparatus;
    placing a closed package unopened in the chamber, the package including at least a first compartment which holds peracetic acid and a second sealed compartment which holds a color indicator;

adding a dilutant to the chamber;

comminuting the wastes and the package in the chamber (i) releasing the peracetic acid and the color indicator into the dilutant to form an anti-microbial solution, the color indicator providing an initial color to the anti-microbial solution which changes color to indicate a completeness of the microbial decontamination procedure, (ii) grinding the medical wastes and the package to a slurry, and (iii) intermixing the anti-microbial solution with all surfaces in the slurry, the anti-microbial solution having a sufficient strength to kill all pathogenic microorganisms in the biological waste;

retaining the anti-microbial solution in contact with the surfaces in the slurry until all pathogenic microorganisms have been killed and the indicator has changed color;

separating the anti-microbial solution from solid components of the slurry.

3. The method as set forth in claim 2 wherein the color indicator includes Gentian Violet.

4. A method of decontaminating infectious wastes, the method comprising:

placing infectious wastes in a chamber containing a grinder;

placing a package which includes a first compartment which holds a first dry reagent and a second compartment which holds a second dry reagent unopened in the chamber, the first dry reagent including an acid precursor and the second dry reagent including a persalt where the precursor and the presalt react to form peracetic acid and at least one of the first and second dry reagents further include a color indicator;

adding a volume of liquid dilutant to the chamber;

comminuting the wastes and the package in the chamber (i) releasing the dry reagents into the dilutant, (ii) comminuting the wastes and the package to a slurry, and during the comminuting, the acid precursor and persalt reacting in situ in the dilutant and the slurry to form a peracetic acid solution, and (iii) intermixing the peracetic acid solution with all surfaces in the slurry, the peracetic acid solution having a sufficient anti-microbial activity to kill all pathogenic microorganisms in the biological waste;

holding the peracetic acid solution in contact with the slurry until the color indicator indicates antimicrobially effective peracetic acid activity.

5. The method as set forth in claim 4 wherein the color indicator includes Gentian Violet.

6. The method as set forth in claim 4 wherein the acid precursor includes acetylsalicylic acid and the persalt includes a perborate, the acetylsalicylic acid and perborate reacting during the comminuting step to form peracetic acid and salicylic acid.

* * * * *